(12) United States Patent
Han

(10) Patent No.: US 7,238,817 B1
(45) Date of Patent: Jul. 3, 2007

(54) DIRECT EPOXIDATION PROCESS

(75) Inventor: Yuanzhang Han, New Hope, PA (US)

(73) Assignee: Lyondell Chemical Technology, L.P., Greenville, DE (US)

( * ) Notice: Subject to any disclaimer, the term of this patent is extended or adjusted under 35 U.S.C. 154(b) by 0 days.

(21) Appl. No.: 11/358,984

(22) Filed: Feb. 22, 2006

(51) Int. Cl.
*C07D 301/03* (2006.01)
*C07D 301/10* (2006.01)

(52) U.S. Cl. .................. 549/538; 549/534
(58) Field of Classification Search .......... 549/534, 549/538
See application file for complete search history.

(56) References Cited

U.S. PATENT DOCUMENTS

| | | | |
|---|---|---|---|
| 2,999,821 A | 9/1961 | Fisher | 260/2.1 |
| 3,351,635 A | 11/1967 | Kollar | 260/348.5 |
| 4,367,342 A | 1/1983 | Wulff et al. | 549/529 |
| 4,410,501 A | 10/1983 | Taramasso et al. | 423/326 |
| 4,469,805 A | 9/1984 | Kofke, Jr. et al. | 502/33 |
| 4,639,259 A | 1/1987 | Pearson | 55/71 |
| 4,833,260 A | 5/1989 | Neri et al. | 549/531 |
| 4,994,589 A | 2/1991 | Notermann | 549/534 |
| 5,194,279 A | 3/1993 | Okel | 426/330 |
| 5,571,421 A | 11/1996 | Tennison et al. | 210/674 |
| 5,623,090 A | 4/1997 | Haruta et al. | 568/360 |
| 5,780,657 A | 7/1998 | Cooker et al. | 549/534 |
| 5,856,534 A | 1/1999 | Cooker et al. | 549/534 |
| 5,965,476 A | 10/1999 | Balducci et al. | 502/67 |
| 6,008,388 A | 12/1999 | Dessau et al. | 549/531 |
| 6,362,349 B1 | 3/2002 | Kuperman et al. | 549/533 |
| 6,498,259 B1 | 12/2002 | Grey et al. | 549/533 |
| 6,646,142 B1 | 11/2003 | Meima et al. | 549/536 |
| 7,138,535 B1 * | 11/2006 | Whitman et al. | 549/533 |
| 2003/0045734 A1 * | 3/2003 | Weisbeck et al. | 549/532 |

FOREIGN PATENT DOCUMENTS

| | | |
|---|---|---|
| BE | 1001038 A7 | 6/1989 |
| EP | 0 132 049 | 6/1984 |
| EP | 0 345 856 | 5/1989 |
| JP | 4-352771 | 12/1992 |

OTHER PUBLICATIONS

R. Szostak, "Non-Aluminosilicate Molecular Sieves", in *Molecular Sieves: Principles of Synthisis and Identification* (1989) 205.
G. Vayssailov, *Catal. Rev.—Sci. Eng.* 39(3). (1997) 209.
K. Tanabe et el., "Definition and Classification of Solid Acids and Bases" In *New Solid Acids and Bases* (1989) 1.
F. Helfferich, *Ion Exchange* (1962) 26.
D. Farrier et al., *J. Colloid Interface Sci.* 69 (2) (1979) 233.
L. Pochhali et al., *J. Indian Chem. Soc.* 54 (9) (1977) 859.
J. Humphrey et al., *Separation Process Technology* (1997) 153.

* cited by examiner

*Primary Examiner*—J. Parsa
(74) *Attorney, Agent, or Firm*—Yuanzhang Han

(57) ABSTRACT

A process is disclosed for reacting an olefin, hydrogen, and oxygen in a reactor in the presence of a catalyst comprising a transition metal zeolite and a noble metal to produce a reaction mixture comprising an epoxide and acidic byproducts. A portion of the reaction mixture is contacted with an adsorbent so that a treated mixture having a reduced amount of byproducts is produced. The treated mixture is recycled back to the reactor. Including an adsorption step should improve the catalyst productivity and epoxide selectivity.

20 Claims, 3 Drawing Sheets

# DIRECT EPOXIDATION PROCESS

FIELD OF THE INVENTION

The invention relates to a process for producing an epoxide from hydrogen, oxygen, and an olefin.

BACKGROUND OF THE INVENTION

Many different methods for the preparation of epoxides have been developed. Commercially, propylene oxide is produced by the chlorohydrin process or hydroperoxidation (see, e.g., U.S. Pat. Nos. 3,351,635 and 4,367,342; EP 0 345 856). Unfortunately, both processes have disadvantages. The chlorohydrin process suffers from the production of a dilute salt stream. The hydroperoxidation process, in which propylene is oxidized with an organic hydroperoxide such as ethylbenzene hydroperoxide or tert-butyl hydroperoxide, produces organic co-products such as t-butyl alcohol or styrene, whose value must be captured in the market place. Ethylene oxide is commercially produced by the direct oxidation of ethylene with oxygen over a silver catalyst. Unfortunately, efforts to epoxidize higher olefins (olefins containing three or more carbons) such as propylene with oxygen in the presence of a silver catalyst have failed to produce a commercial process (see, e.g., U.S. Pat. Nos. 5,856,534, 5,780,657 and 4,994,589).

Recent efforts have focused on the direct epoxidation of higher olefins with oxygen and hydrogen. For example, the reaction may be performed in the presence of a catalyst comprising gold and a titanium-containing carrier (see, e.g., U.S. Pat. Nos. 5,623,090, 6,362,349, and 6,646,142), or a catalyst containing palladium and a titanium zeolite (see, e.g., JP 4-352771).

Mixed catalyst systems for olefin epoxidation with hydrogen and oxygen have also been disclosed. For example, Example 13 of JP 4-352771 describes the use of a mixture of titanosilicate and Pd-on-carbon for propylene epoxidation. U.S. Pat. No. 6,008,388 describes a catalyst comprising a noble metal and a titanium or vanadium zeolite, but additionally teaches that the Pd can be incorporated into a carrier before mixing with the zeolite. The catalyst carriers disclosed include silica, alumina, and activated carbon.

Unfortunately, undesirable reactions also occur in these epoxidation processes. For example, the produced epoxide tends to react with solvents (e.g., water, methanol) to form glycols and/or glycol ethers. These side reactions are catalyzed by acids, which are formed as byproducts during the epoxidation. U.S. Pat. No. 6,498,259 discloses the epoxidation of an olefin with hydrogen and oxygen in a solvent containing a buffer in the presence of a catalyst mixture containing a titanium zeolite and a noble metal catalyst. Although a buffer can reduce the formation of the byproducts, it tends to complicate product purification. For example, a buffer can cause the fouling of distillation columns due to salt formation.

In sum, new processes for olefin epoxidation with reduced byproduct formation are needed.

SUMMARY OF THE INVENTION

The invention is a process comprising reacting an olefin, hydrogen, and oxygen in the presence of an epoxidation catalyst comprising a transition metal zeolite and a noble metal to produce a reaction mixture comprising an epoxide and acidic byproducts. A portion of the reaction mixture is contacted with an adsorbent so that a treated mixture having a reduced amount of acidic byproducts is produced, and thereafter the treated mixture is recycled back to the reaction. Including an adsorption step is expected to improve catalyst productivity and epoxide selectivity.

DETAILED DESCRIPTION OF THE INVENTION

Figure 1:
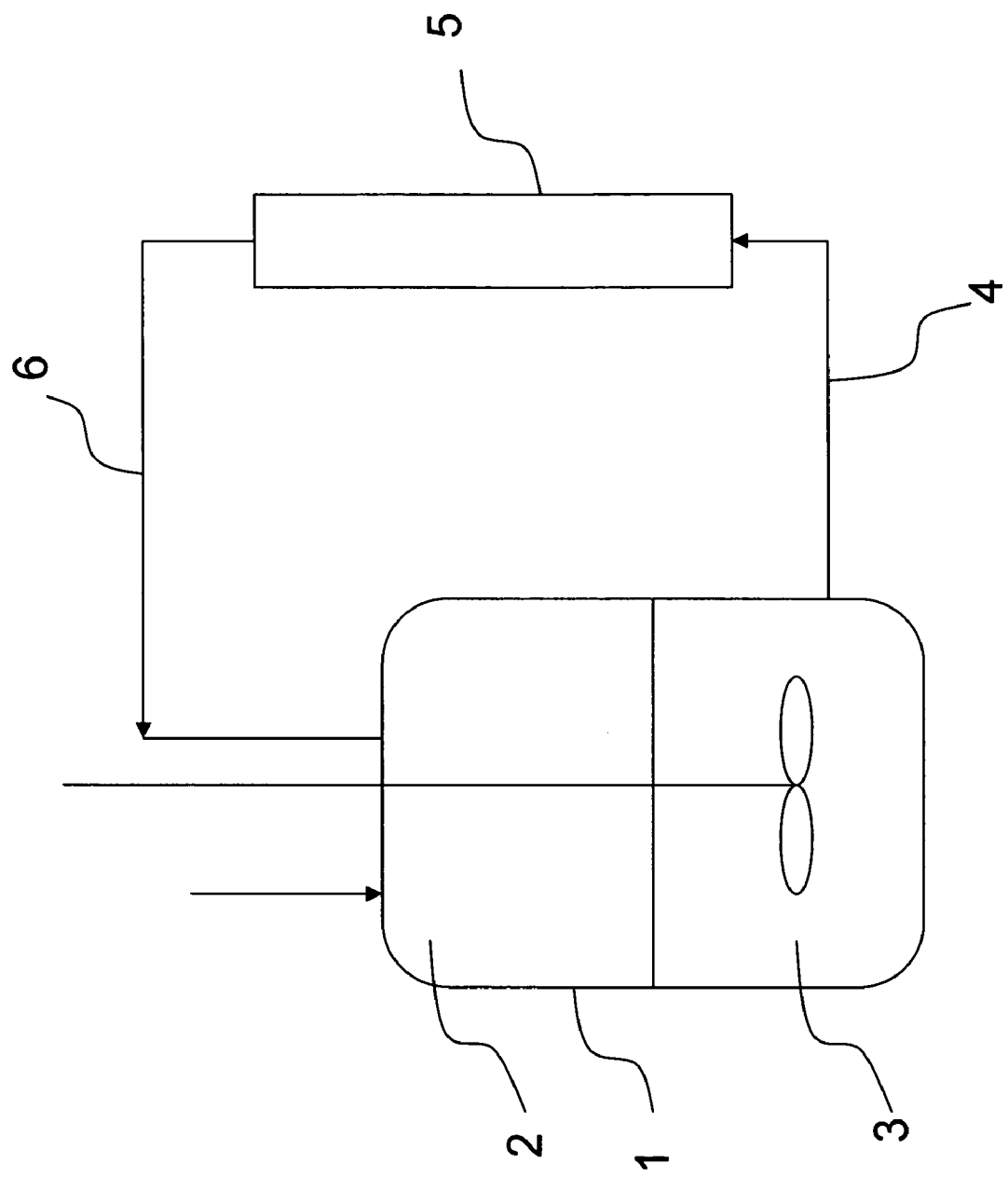
FIG. 1 is a schematic presentation of one embodiment of the present invention including a batch stirred tank reactor for epoxidation and an adsorption bed.

The process of the invention employs an epoxidation catalyst comprising a transition metal zeolite. Zeolites generally contain one or more of Si, Ge, Al, B, P, or the like, in addition to oxygen. A transition metal zeolite (e.g., titanium zeolite, vanadium zeolite) is a crystalline material having a porous molecular sieve structure and containing a transition metal. A transition metal is a Group 3-12 element. The first row of these includes elements from Sc to Zn. Preferred transition metals are Ti, V, Mn, Fe, Co, Cr, Zr, Nb, Mo, and W. Particularly preferred are Ti, V, Mo, and W. Most preferred is Ti. The type of transition metal zeolite employed depends upon a number of factors, including the size and shape of the olefin to be epoxidized. For example, it is especially advantageous to use titanium silicalite-1 (TS-1, a titanium silicalite having an MFI topology analogous to that of the ZSM-5 aluminosilicate) for the epoxidation of propylene. For a bulky olefin such as cyclohexene, larger pore zeolites may be preferred.

Suitable titanium zeolites include titanium silicates (titanosilicates). Preferably, they contain no element other than titanium, silicon, and oxygen in the lattice framework (see R. Szostak, "Non-aluminosilicate Molecular Sieves," in *Molecular Sieves: Principles of Synthesis and Identification* (1989), Van Nostrand Reinhold, pp. 205-282). Small amounts of impurities, e.g., boron, iron, aluminum, phosphorous, copper, and the like, and mixtures thereof, may be present in the lattice. The amount of impurities is preferably less than 0.5 weight percent (wt. %), more preferably less than 0.1 wt. %. Preferred titanium silicates will generally have a composition corresponding to the following empirical formula: $xTiO_2 \cdot (1-x)SiO_2$, where x is between 0.0001 and 0.5000. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. Particularly preferred titanium zeolites include the class of molecular sieves commonly known as titanium silicalites (see *Catal. Rev.-Sci. Eng.* 39(3) (1997) 209). Examples of these include TS-1, TS-2 (having an MEL topology analogous to that of the ZSM-11 aluminosilicate), and TS-3 (as described in Belgian Pat. No. 1,001,038). Titanium zeolites having framework structures isomorphous to zeolite beta, mordenite, and ZSM-12 are also suitable for use.

The epoxidation catalyst comprises a noble metal. Suitable noble metals include, e.g., gold, silver, platinum, palladium, iridium, ruthenium, rhenium, rhodium, osmium, and mixtures thereof. Preferred noble metals are Pd, Pt, Au, Re, Ag, and mixtures thereof. While any of the noble metals can be utilized, either alone or in combination, palladium and gold are particularly desirable. Typically, the amount of noble metal present in the epoxidation catalyst will be in the range of from 0.01 to 20 wt. %, preferably 0.1 to 5 wt. %.

The noble metal and the transition metal zeolite may be on a single particle or on separate ones. For example, the noble metal may be supported on the transition metal zeolite. Alternatively, the epoxidation catalyst may comprise a mixture of a transition metal zeolite and a noble metal. The noble metal may be essentially elemental (e.g., colloidal Pd), or it may be supported on a carrier. Suitable carriers for the supported noble metal include carbons, titanias, zirconias, niobias, silicas, aluminas, silica-aluminas, titania-silicas, zirconia-silicas, niobia-silicas, ion-exchange resins, and the like, and mixtures thereof.

The manner in which the noble metal is incorporated into the epoxidation catalyst is not critical. For example, the noble metal may be supported on the transition metal zeolite or other carriers by impregnation, ion exchange, adsorption, precipitation, or the like.

There are no particular restrictions regarding the choice of the noble metal compound or complex used as the source of the noble metal. Suitable compounds include nitrates, sulfates, halides (e.g., chlorides, bromides), carboxylates (e.g., acetate), and amine or phosphine complexes of noble metals (e.g., palladium(II) tetraammine bromide, tetrakis(triphenylphosphine) palladium).

Similarly, the oxidation state of the noble metal is not critical. Palladium, for instance, may be in an oxidation state anywhere from 0 to +4 or any combination of such oxidation states. To achieve the desired oxidation state or combination of oxidation states, the noble metal compound after being introduced in the epoxidation catalyst may be fully or partially pre-reduced. Satisfactory catalytic performance can, however, be attained without any pre-reduction.

The weight ratio of the transition metal zeolite:noble metal is not particularly critical. However, a transition metal zeolite:noble metal ratio of 0.01-100 (grams of transition metal zeolite per gram of noble metal) is preferred.

The epoxidation catalyst is preferably in the form of a suspension or fixed-bed. The process may be performed in a continuous flow, semi-batch, or batch mode. It is advantageous to work at a pressure of 1-200 bars. Epoxidation reaction according to the invention is carried out at a temperature effective to achieve the desired olefin epoxidation, preferably at temperatures in the range of 0-200° C., more preferably, 20-150° C. Preferably, at least a portion of the reaction mixture is liquid under the reaction conditions.

An olefin is required. Suitable olefins include any olefin having at least one carbon-carbon double bond, and generally from 2 to 60 carbon atoms. Preferably, the olefin is an acyclic alkene of from 2 to 30 carbon atoms. The process of the invention is particularly suitable for epoxidizing $C_2$-$C_6$ olefins. More than one double bond may be present in the olefin molecule, as in a diene or triene. The olefin may be a hydrocarbon or it may contain functional groups such as halide, carboxyl, hydroxy, ether, carbonyl, cyano, nitro groups, or the like. The process of the invention is especially useful for converting propylene to propylene oxide.

Oxygen and hydrogen are required. Although any sources of oxygen and hydrogen are suitable, molecular oxygen and molecular hydrogen are preferred. The molar ratio of hydrogen to oxygen can usually be varied in the range of $H_2$:$O_2$=1:100 to 5:1 and is especially favorable at 1:5 to 2:1. The molar ratio of oxygen to olefin is usually 1:1 to 1:20, and preferably 1:1.5 to 1:10. Relatively high oxygen to olefin molar ratios (e.g., 1:1 to 1:3) may be advantageous for certain olefins.

In addition to the olefin, oxygen, and hydrogen, an inert gas may be preferably used. Suitable inert gases include nitrogen, helium, argon, and carbon dioxide. Saturated hydrocarbons with 1-8, especially 1-6, and preferably 1-4 carbon atoms, e.g., methane, ethane, propane, and n-butane, are also suitable. Nitrogen and saturated $C_1$-$C_4$ hydrocarbons are preferred inert gases. Mixtures of the listed inert gases can be used. The molar ratio of olefin to inert gas is usually in the range of 100:1 to 1:10 and especially 20:1 to 1:10.

The amount of transition metal zeolite used may be determined on the basis of the molar ratio of the transition metal contained in the transition metal zeolite to the olefin that is supplied per unit time. Typically, sufficient transition metal zeolite is present to provide a transition metal/olefin per hour molar feed ratio of from 0.0001 to 0.1.

The epoxidation step preferably uses a solvent. Suitable solvents are liquid under the reaction conditions. They include, for example, oxygen-containing hydrocarbons such as alcohols, aromatic and aliphatic solvents such as toluene and hexane, chlorinated aromatic and aliphatic solvents such as chlorobenzene and methylene chloride, nitriles such as acetonitrile, carbon dioxide, and water. Suitable oxygenated solvents include alcohols, ethers, esters, ketones, carbon dioxide, water, and the like, and mixtures thereof. Preferred oxygenated solvents include water and $C_1$-$C_4$ alcohols such as methanol, ethanol, isopropanol, and tert-butanol, and mixtures thereof. Fluorinated alcohols can be used.

The epoxidation step produces a reaction mixture comprising an epoxide and acidic byproducts. An acidic byproduct is any compound that can ionize in aqueous solution and thereby make the solution acidic (pH<7). Acidic byproducts formed in the process might include carbonic acid (or $CO_2$), formic acid, acetic acid, propionic acid, acrylic acid, HCl, $HNO_3$, HBr, $NH_4^+$ salts, and the like. Acidic byproducts can catalyze reactions of epoxides with solvents (e.g., water, alcohol) to form glycols and/or glycol ethers. It is desirable to minimize such reactions.

The present process also comprises contacting a portion of the reaction mixture with an adsorbent to produce a treated mixture having a reduced amount of byproducts. The adsorbent is any solid that is capable of removing acidic compounds from a solution or a mixture (e.g., a gas liquid mixture). Suitable adsorbents for the present process include basic ion-exchange resins (e.g., organic resins containing alkylamines, alkylammonium hydroxide), molecular sieves, aluminas, silicas, titanias, activated carbons, alkali metal oxides, alkaline earth metal oxides, mixed oxides (e.g., MgO-silica, CaO-alumina), supported alkali or alkaline earth metal oxides (e.g., CaO supported on carbons, silicas, aluminas, or zeolites), alkaline earth metal salts (e.g., calcium carbonate, magnesium carbonate), clays, and the like, and mixtures thereof. For examples of adsorbents, see K. Tanabe, et al., "Definition and Classification of Solid Acids and Bases" in *New Solid Acids and Bases*, Elsevier Science Publishing Company, Inc. (1989), pp. 1-4; *Ion Exchange*, Friedrich Helfferich, McGraw-Hill Book Company, Inc. (1962), pp. 26-71; *J. Colloid Interface Sci.* 69(2) (1979) 233; *J. Indian Chem. Soc.* 54(9) (1977) 859; EP 132049; U.S. Pat. Nos. 4,639,259, 4,469,805 and 5,571,421. Inorganic materials with tethered organic bases (e.g., silica having tethered alkylamines, or alkylammonium hydroxides as described in U.S. Pat. No. 5,194,279) can also be used. Preferred adsorbents include basic ion-exchange resisn, aluminas, CaO, MgO, activated carbons, and the like, and mixtures thereof. Basic ion-exchange resins are most preferred.

Typically, the adsorbent is charged in one or more adsorption vessels and the reaction mixture is contacted with the adsorbent within the adsorption vessel(s). The adsorption may be performed in a continuous flow or batch mode. For example, when the adsorption is carried out in a continuous flow, a stream of reaction mixture is continuously withdrawn from the reactor, fed to the adsorption vessel(s), and contacted with the adsorbent. The absorbent may be in a slurry or fixed-bed (adsorption bed). Preferably, it is in a fixed-bed (see J. Humphrey, et al., *Separation Process Technology*, McGraw-Hill (1997), pp. 153-157). One or more adsorption beds may be used. When more than one bed is used, they may be used in parallel (e.g., see FIG. 3) or in series. The pressure and temperature at which the adsorption is carried out is not critical, although it may be advantageous to perform the adsorption at a temperature that is lower than the reaction temperature.

A treated mixture having a reduced amount of acidic byproducts is produced from the adsorption step. The process of the invention comprises recycling the treated mixture back to the epoxidation. In a down-flow fixed-bed reactor, the reaction mixture is preferably taken from the bottom of the reactor and the treated mixture is fed to the top of the reactor (see FIGS. 2 and 3).

In one embodiment of the invention, the epoxidation reaction is carried out in a batch stirred tank reactor and the adsorption is performed with an adsorption bed in a continuous flow mode, as shown in FIG. 1. Reactants (olefin, hydrogen, and oxygen), the epoxidation catalyst, and inert gas and/or solvent if used, are charged to reactor 1. The reactor contents are either in the gas phase 2 or liquid phase 3. The reactor is maintained at desired temperature and pressure. A portion of the liquid mixture is continuously withdrawn through line 4 from the liquid phase 3, and is fed to the adsorption bed 5 at the bottom of the bed. The treated mixture exits the adsorption bed from the top and recycles back to reactor 1 through line 6. A chiller may be installed in line 4 so that the liquid reaction mixture may be cooled to a lower temperature before being fed to the adsorption bed 5. The flow rate of the liquid reaction mixture from the reactor to the adsorption bed is not critical as long as it effectively removes acids from the mixture. Typically the flow rate ranges from 0.1V to 10V per hour, where V is the volume of the liquid reaction mixture in the reactor.

Figure 2:
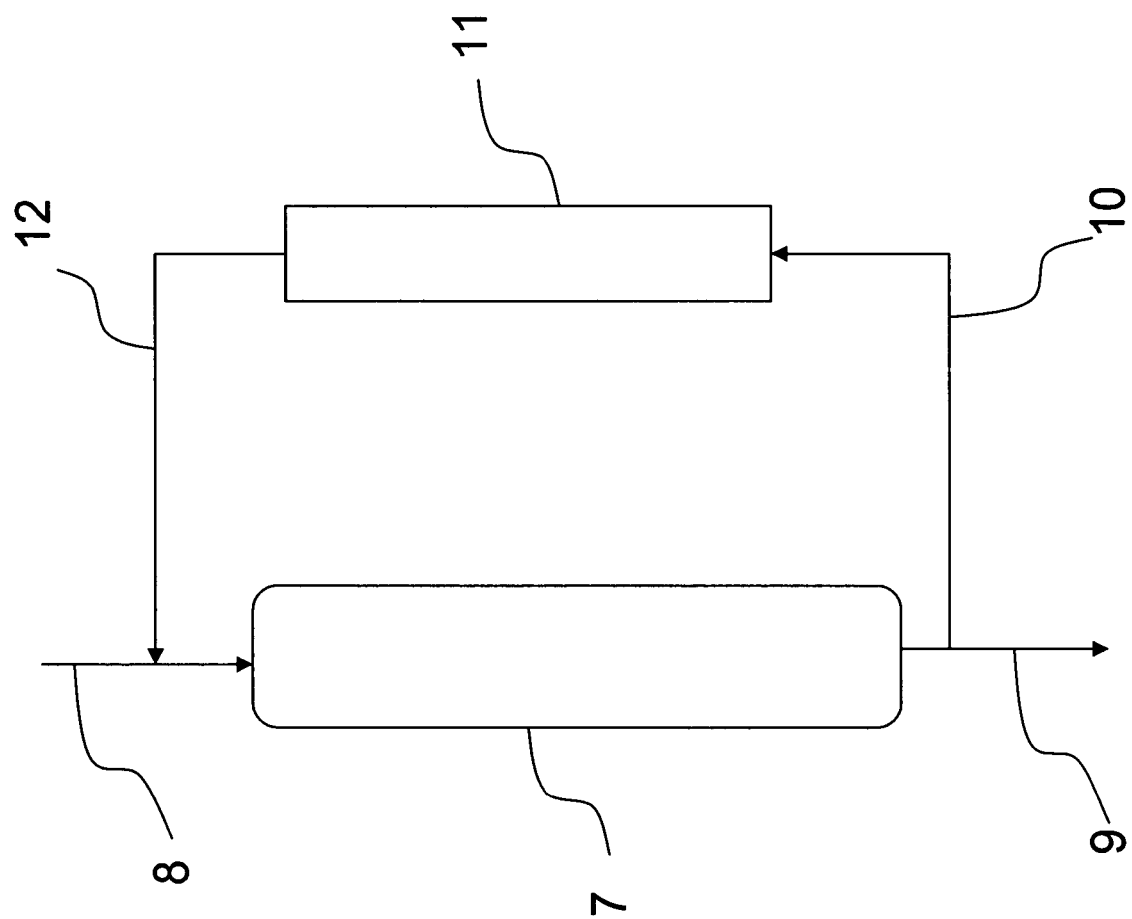
FIG. 2 is a schematic presentation of another embodiment of the present invention including a fixed-bed epoxidation reactor and an adsorption bed.

In another embodiment, the epoxidation is carried out in a fixed-bed reactor, and the adsorption is performed in continuous flow mode, as shown in FIG. 2. The solid epoxidation catalyst is charged to reactor 7. Reactants, including olefin, hydrogen, oxygen, and inert gas and/or solvent if used, are continuously fed to reactor 7 at the top of the reactor through line 8. A product stream flows out of the reactor continuously from the bottom of the reactor through line 9. A portion of the reaction mixture is continuously withdrawn from the bottom of the reactor though line 10 and is fed to bottom of the adsorption bed 11. The treated mixture exits the adsorption bed at the top of the bed and recycles back to reactor 7 through line 12. A chiller may be installed in line 10 so the reaction mixture may be cooled to a lower temperature before fed to the adsorption bed. Typically the flow rate of the reaction mixture in line 10 ranges from 0.1V to 10V per hour, where V is the volume of the reactor 7.

Figure 3:
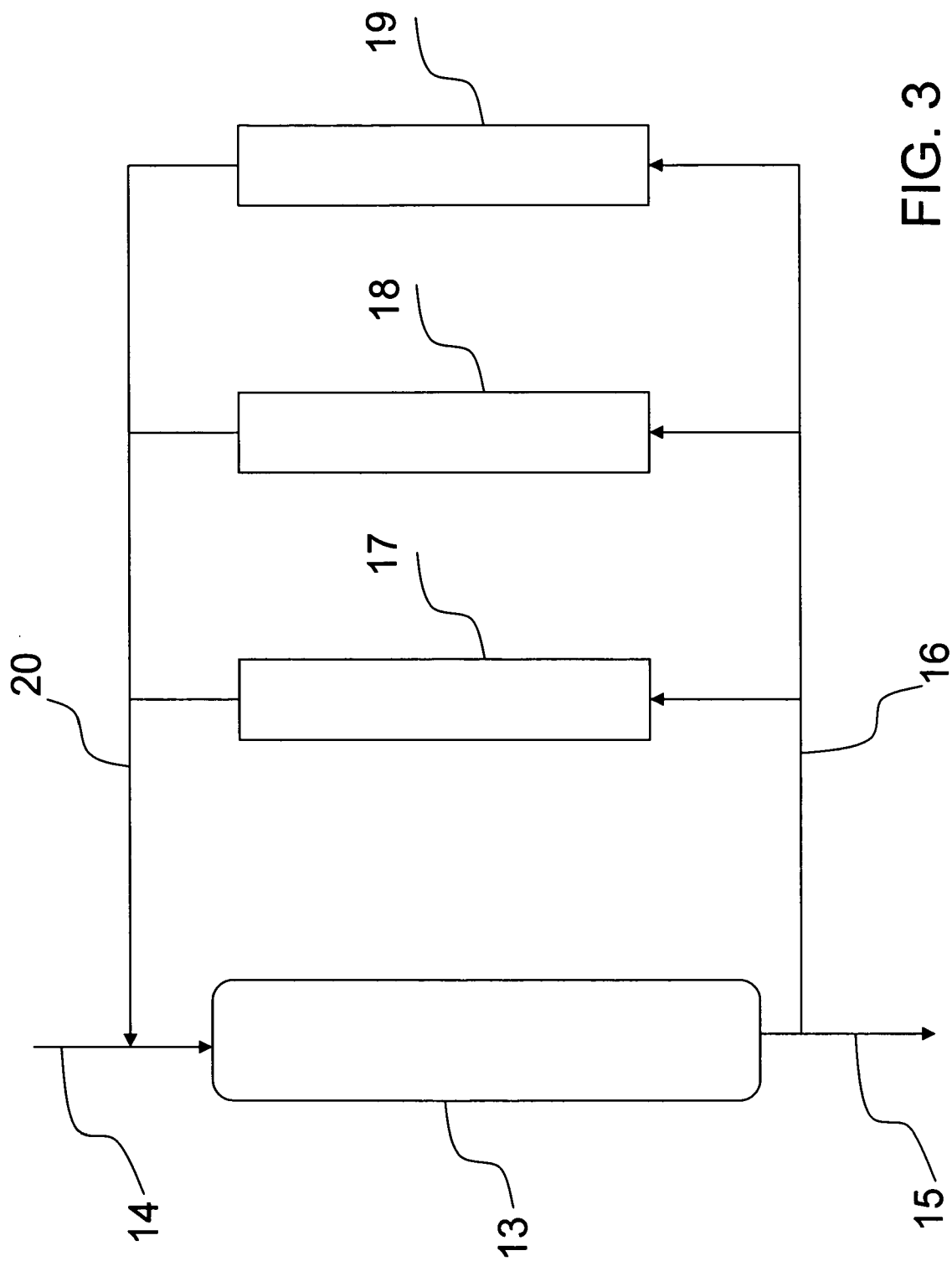
FIG. 3 shows a similar process to that in FIG. 2, except with three adsorption beds in parallel.

The scheme in FIG. 3 is similar to that in FIG. 2, except that three parallel adsorption beds 17, 18, and 19 are used.

Generally, the adsorption capacity (the amount of certain byproducts that an adsorbent can adsorb) is limited. As a result, after a certain amount of reaction mixture passes through the adsorbent, it gets "exhausted" and can no longer remove acidic byproducts from the stream. An exhausted adsorbent needs to be either replaced with fresh adsorbent or regenerated to restore its adsorption capacity. The regeneration is usually performed by heating the adsorbent remove the adsorbed materials, or washing the exhausted adsorbent with a solvent or a solution. Inorganic adsorbents (e.g., silicas, aluminas, CaO, zeolites, clays) may be regenerated by heating or calcining in the presence of oxygen-containing gas to burn off the organics accumulated on the adsorbent. Basic resins, on the other hand, are generally regenerated by washing with a base solution (e.g., $Na_2CO_3$, $NaHCO_3$, NaOH, KOH, ammonium hydroxide solutions in water, alcohols, ketones, and the like) due to their limited thermal stability (U.S. Pat. No. 2,999,821). Preferably, the adsorbent is further washed with a solvent (e.g., water, alcohols, ketones, aromatic compounds, halogenated solvents, nitrites, water, carbon dioxide) to remove metal ions (e.g., $Na^+$, $K^+$) before the bed is used in the process. The regeneration may be carried out in a slurry or fixed-bed. It may be carried out off-line (where the exhausted adsorbent is removed from an adsorption vessel, regenerated elsewhere, and recharged to the adsorption vessel), or on-line (where the regeneration of the exhausted adsorbent is conducted in the adsorption vessel). In a continuous epoxidation process, more than one adsorption vessel is preferably used, which allows the on-line regeneration of the exhausted adsorbent in one vessel while the other vessel(s) are in service, as in the case of FIG. 3.

Because the adsorption step removes undesirable acidic byproducts from the reaction mixture, its use should improve the rate and selectivities of the epoxidation reaction.

Following examples merely illustrate the invention. Those skilled in the art will recognize many variations that are within the spirit of the invention and scope of the claims.

COMPARATIVE EXAMPLE 1

Epoxidation of Propylene

Titanium silicalite-1 (TS-1) samples are prepared by following procedures disclosed in U.S. Pat. Nos. 4,410,501 and 4,833,260. Spray dried TS-1 catalyst (containing about 20 wt. % silica binder) is prepared by following procedures disclosed in U.S. Pat. No. 5,965,476. Carbon supported Pd (Pd/C) is prepared by following the procedure in Example 2 of U.S. Pat. No. 6,498,259. It is expected to contain 0.4 wt. % Pd.

A 300-mL stainless steel reactor is charged with Pd/C (0.2 g) and spay dried TS-1 powder (0.5 g), water (13 g), and methanol (100 g). The reactor is then pressurized to 300 psig with a feed gas consisting of 2 volume percent (vol. %) hydrogen, 4 vol. % oxygen, 5 vol. % propylene, 0.5 vol. % methane, and the balance nitrogen. The pressure in the reactor is maintained at 300 psig via a back pressure regulator with the feed gases passed continuously through the reactor at 1600 mL/min (measured at 23° C. and 1 atmosphere pressure). In order to maintain a constant solvent level in the reactor during the run, the oxygen, nitrogen and propylene feeds are passed through a 2-L stainless steel vessel (saturator) preceding the reactor containing 1.5 L of methanol. The reaction mixture is heated to 60° C. while it is stirred at 1500 rpm. The gaseous effluent is analyzed by an on-line gas chromatograph (GC) and the liquid analyzed by off-line GC at the end of the run. The products formed include propylene oxide (PO), propane, and derivatives of propylene oxide such as propylene glycol, propylene glycol monomethyl ethers, dipropylene glycol, and dipropylene glycol methyl ethers.

EXAMPLE 2

Epoxidation of Propylene with Circulating Adsorption Bed

The procedure in Example 1 is repeated except that an adsorption bed (internal diameter, 0.5 inch; height, 12 inches) charged with Amberlyst A26-OH (obtained from Rohm & Haas) is installed. A liquid stream of reaction mixture is withdrawn from the reactor through a filter with a pump, passed through the bed at a flow rate of 10 mL/min (up flow), and fed back to the reactor. Improved catalyst productivity and selectivity to propylene oxide should be obtained compared to Example 1.

I claim:
1. An epoxidation process comprising:
   (a) reacting an olefin, hydrogen, and oxygen in the presence of an epoxidation catalyst comprising a transition metal zeolite and a noble metal to produce a reaction mixture comprising an epoxide and acidic byproducts;
   (b) contacting a portion of the reaction mixture with an adsorbent to produce a treated mixture having a reduced amount of acidic byproducts; and
   (c) recycling the treated mixture to step (a).
2. The process of claim 1 wherein the noble metal is supported on the transition metal zeolite.
3. The process of claim 2 wherein the noble metal is selected from the group consisting of palladium, platinum, gold, rhenium, silver, and mixtures thereof.
4. The process of claim 2 wherein the transition metal zeolite is a titanium zeolite.
5. The process of claim 1 wherein the noble metal is supported on a carrier.
6. The process of claim 5 wherein the carrier is selected from the group consisting of carbons, titanias, zirconias, niobias, silicas, aluminas, silica-aluminas, titania-silicas, zirconia-silicas, niobia-silicas, ion-exchange resins, and mixtures thereof.
7. The process of claim 5 wherein the transition metal zeolite is a titanium zeolite.
8. The process of claim 5 wherein the noble metal is selected from the group consisting of palladium, platinum, gold, rhenium, silver, and mixtures thereof.
9. The process of claim 1 wherein the epoxidation reaction is performed in the presence of a solvent.
10. The process of claim 9 wherein the solvent is selected from the group consisting of alcohols, ethers, esters, ketones, carbon dioxide, water, and mixtures thereof.
11. The process of claim 1 wherein the adsorbent is selected from the group consisting of basic ion-exchange resins, aluminas, calcium oxide, magnesium oxide, activated carbons, and mixtures thereof.
12. The process of claim 1 wherein the adsorbent is a basic ion-exchange resin.
13. The process of claim 1 wherein the adsorbent is in a fixed-bed.
14. The process of claim 1 wherein the adsorbent is in a slurry.
15. The process of claim 1 wherein step (b) is performed in continuous flow mode.
16. The process of claim 1 wherein step (b) is performed in batch mode.
17. The process of claim 1 wherein the adsorbent is regenerated on-line.
18. The process of claim 1 wherein the adsorbent is in multiple adsorption vessels.
19. The process of claim 1 wherein the olefin is propylene.
20. The process of claim 19 wherein the adsorbent is a basic ion-exchange resin.

\* \* \* \* \*